United States Patent [19]

Sozzi

[11] Patent Number: 4,870,020
[45] Date of Patent: Sep. 26, 1989

[54] PREPARATION OF COMPOSITIONS INCLUDING ACID-RESISTANT BIFIDOBACTERIA

[75] Inventor: Tomaso Sozzi, Lausanne, Switzerland

[73] Assignee: Nestec S.A., Vevey, Switzerland

[21] Appl. No.: 825,195

[22] Filed: Feb. 3, 1986

[30] Foreign Application Priority Data

Feb. 28, 1985 [CH]  Switzerland ............................ 916/85

[51] Int. Cl.$^4$ .......................... C12N 1/20; C12P 7/56; C12P 7/54
[52] U.S. Cl. ....................... 435/252.1; 435/139; 435/140; 426/43; 426/61
[58] Field of Search ..................... 435/253, 139, 252.1; 426/43, 61

[56] References Cited

U.S. PATENT DOCUMENTS

| | | | |
|---|---|---|---|
| 4,091,117 | 0/1978 | Mutai et al. | 426/43 |
| 4,187,321 | 2/1980 | Mutai et al. | 426/43 |
| 4,588,595 | 5/1986 | Okonogi et al. | 426/43 |
| 4,601,985 | 7/1986 | Okonogi et al. | 435/253 |

Primary Examiner—Thomas G. Wiseman
Assistant Examiner—Charles L. Patterson, Jr.
Attorney, Agent, or Firm—Vogt & O'Donnell

[57] ABSTRACT

Acid resistant bifidobacteria, particularly the strains *Bifidobacterium infantis* CNCM I-372, *Bifidobacterium bifidum* CNCM I-373 and *Bifidobacterium breve* CNCM I-374, are cultured in a semisynthetic or synthetic lactic medium. The culture compositions are resistant to oxygen and acid and have a survival level of at least 1:10 after 30 days at a pH of 4.0 at 5° C. and thus are utilized in acidified food products, such as acidified milks and yogurts, having a pH of from 4.0 to 4.6.

12 Claims, No Drawings

PREPARATION OF COMPOSITIONS INCLUDING ACID-RESISTANT BIFIDOBACTERIA

BACKGROUND OF THE INVENTION

This invention relates to a process for the preparation of a culture of acid-resistant bifidobacteria, to the culture thus obtained and to the use of this culture for the preparation of food products containing acid-resistant bifidobacteria.

Bifidobacteria are known as indicators or even guarantors of a healthy intestinal flora in sucklings. However, their use in a viable form for dietetic purposes, for example in products of the acidified milk type, such as for example yogurts, is attended by known difficulties, such as their sensitivity to oxygen and to acid. Certain strains have already been proposed which have a high resistance to oxygen and even a considerable resistance to acid. However, the most resistant known bifidobacteria survive hardly more than a few days or even a week at the pH-values shown by acidified milks, such as yogurts for example, during their storage in refrigerators.

SUMMARY OF THE INVENTION

The object of the present invention is to provide cultures of acid-resistant bifidobacteria which survive for long periods in food products, such as acidified milks, particularly yogurts.

To this end, the process according to the invention is characterized in that a strain of bifidobacteria having a survival level at least 1:10 after 30 d at pH 4.0/5° C. is cultivated in a semisynthetic or synthetic lactic medium.

Similarly, the use of the culture obtained by the process according to the invention is characterized in that the culture is added to a food product during its preparation.

It has been found that it is possible to find strains of bifidobacteria of which the resistance to acid is completely surprising by comparison with what has hitherto been known or accepted and that it is possible to prepare cultures thereof suitable for use in the preparation of food products having an acid pH, such as acidified milks for example, in which they show a remarkable survival level.

In the context of the invention, the expression "survival level" is used to designate the number of bacteria which survive in a culture or a food product after a period of storage or after a particular treatment in relation to the original number of living bacteria in the culture or the product. The survival level is expressed by a ratio, for example 1:10.

Similarly, the expression "lactic medium" is used to designate a medium based essentially on whole or skimmed animal or vegetable milk. The expression "semisynthetic medium" designates a medium based on animal or vegetable milk which has been supplemented by a substantial quantity of nutritive elements or growth factors for the bifidobacteria. The expression "synthetic medium" designates a medium formed essentially by the combination of nutritive elements and growth factors of various types, such as, for example, the medium de Man, Rogasa and Sharpe agar, hereinafter "MRS", well known to the expert.

Finally, since bifidobacteria are difficult to count in practice when they are mixed with streptococci, which is particularly the case when the bifidobacteria are used in the preparation of food products of the acidified milk type, a particular method of counting bifidobacteria has been developed and used within the scope of the invention. It is described hereinafter after just before the Examples.

DETAILED DESCRIPTION OF THE INVENTION

The process according to the invention is carried out using a semisynthetic or synthetic lactic medium. It is possible with advantage to use a whole or skimmed cow's milk to which may be added approximately 0.1 to 2% by weight of yeast extract and 0.1 to 2% by weight of glucose, a whole or defatted soya milk, namely an aqueous extract of whole beans or defatted flakes, or a synthetic medium, such as the medium MRS for example. After the medium has been pasteurized or sterilized, it may be inoculated with approximately 3 to 10% by volume of an inoculum containing per $cm^3$ approximately $10^8$ to $10^{10}$ of a strain of bifidobacteria having a survival level of at least 1:10 after 30 d at pH 4.0/5° C.

The bifidobacteria strains preferably are selected from the group comprising *Bifidobacterium infantis* CNCM I-372, *Bifidobacterium bifidum* CNCM I-373 and *Bifidobacterium breve* CNCM I-374. These three strains were lodged on the Nov. 21, 1984 under the Budapest Treaty in the Collection Nationale de Cultures de Microorganismes (CNCM) of the Institut Pasteur, 25 rue du Docteur Roux, 75724-Paris Cedex 15, France, where they were subsequently given the Nos. I-372, I-373 and I-374. They are distinguished not only by their remarkable resistance to acid, but also by a sufficient resistance to oxygen for allowing the process according to the invention to be performed and the use according to the invention carried out without strict anaerobiosis. Finally, they show these qualities of resistance to oxygen and to acid to similar degrees. Likewise, their general characteristics such as, in particular, their growth rates, are similar. By virtue of these similarities, cultures of these three strains are interchangeable within the scope of the use according to the invention. Accordingly, they may be used in a traditional system of rotation which is intended to limit the dangers of destruction of the bifidobacteria by associated phages.

The bifidobacteria strains preferably are cultivated at a temperature favorable to the development of the bifidobacteria, i.e., at a temperature of from about 35° to 42° C. for the period of time necessary for the number of bacteria in the culture to grow to an amount of from approximately $10^8$ to $10^{10}/cm^3$, i.e., for approximately 8 to 16 h.

In order to carry out the use of the culture obtained in accordance with the invention, the culture may be added to a food product during its preparation, during a fermentation stage, or during a supplementation stage for example, depending on whether it is desired to acidify the food product in question with the culture itself or whether it is preferred to acidify the food product before addition of the culture, for example.

Thus, in one preferred form of use, the culture is added to a pasteurized or sterilized, animal or vegetable milk and the milk is acidified to pH 4.0–4.6 by fermentation with the culture. The culture may be added to the milk in a quantity of approximately 3 to 10% by volume and fermentation may be allowed to take place for approximately 8 to 16 h at 35° to 42° C. Acidified milks rich in acid-resistant bifidobacteria are thus obtained, the viscosity of which may be adjusted by varying the dry matter content of the starting milk.

In another preferred embodiment, the culture is added to an acidified milk having a pH of from 4.0 to 4.6. In this embodiment, the milk, which may be animal or vegetable milk, may have been acidified after pasteurization or sterilization by addition of lactic acid, for example, or by fermentation with lactic ferments, such as cultures of yogurt for example. Acidified milks rich in acid-resistant bifidobacteria are obtained in this way, the viscosity of which may be varied between that of an aqueous beverage and that of a stirred yogurt according to the dry matter content of the starting milk.

EXAMPLES

The invention is illustrated by the following Examples which are preceded by a description of the particular method of counting the amount of bifidobacteria which has been developed and used within the scope of the present invention.

Counting Method

A traditional method of counting germs comprises taking a sample of the culture or product to be examined, diluting the sample in aqueous medium, cultivating a fraction of the diluted sample on an MRS agar medium under anaerobic conditions, counting the colonies which have issued from the bacteria on the agar and calculating the original number as a function of the dilution factor.

However, the bifidobacteria are generally mixed with a large number or even an excess of streptococci when they are used in the preparation of food products of the acidified milk type. Now, bifidobacteria give rise on the MRS agar to grey-white colonies which are very difficult to distinguish from the colonies produced by streptococci which are the same size, but white. If the traditional method described above is used for counting bifidobacteria mixed with streptococci, a microscope has to be used and in no way is it possible to count the bifidobacteria when their number is smaller by 2 to 3 powers of ten than the number of streptococci.

It is for this reason that a particular method has been developed to enable the number of bifidobacteria to be counted easily and reliably, irrespective of the number of streptococci with which they are mixed in the sample to be examined.

The counting method according to the invention comprises taking a sample of the culture or product to be examined, diluting the sample in aqueous medium, cultivating a fraction of the diluted sample under anaerobic conditions on a modified MRS agar medium by adding nafcillin thereto in a quantity of 0.1 $\mu$g of nafcillin per cm$^3$ of medium, counting the colonies which have issued from the bacteria on the agar and calculating their original number as a function of the dilution factor.

It has been found that, in a concentration of approximately 0.02 to 0.1 $\mu$g per cm$^3$ of medium, nafcillin completely inhibits the growth of streptococci and of *Lactobacillus bulgaricus*, but has no measurable effect upon the growth of bifidobacteria.

EXAMPLE 1

To 3 liters of skimmed cow's milk are added 1% by weight of yeast extract and 1% by weight of glucose. The milk is pasteurized at 90° C. for 30 minutes and then cooled to 37° C. It is then inoculated with 5% by volume of an inoculum containing per cm$^3$ approximately 10$^9$ living *Bifidobacterium infantis* CNCM I-372 and incubated for 10 h at 37° C. A culture containing 5×10$^9$ living germs of *B. infantis* per cm$^3$ is obtained.

0.8% by volume of the culture thus obtained is added to a pasteurized skimmed cow's milk acidified to pH 4.0 with lactic acid. This milk is stored in a refrigerator at 5° C. and the number of living germs of *B. infantis* which it contains is counted for 0 d, 7 d and 40 d. The numbers are, respectively, 3.80×10$^7$, 3.67×10$^7$ and 2.59×10$^7$ per cm$^3$ of acidified milk. In other words, the survival level of the strain *B. infantis* CNCM I-372 is substantially 10:10 after 7 d and approximately 7:10 after 40 d at pH 4.0/5° C.

EXAMPLE 2

The procedure is as described in Example 1, except that *Bifidobacterium bifidum* CNCM I-373 is cultivated instead of *B. infantis* I-372.

A culture containing 1.0×10$^9$ living *B. bifidum* per cm$^3$ is obtained.

In the storage tests in acidified milk at pH 4.0/5° C., 0.76×10$^7$, 0.58×10$^7$ and 0.46×10$^7$ living *B. bifidum* per cm$^3$ of acidified milk are counted after 0 d, 7 d and 40 d, respectively. In other words, the survival level of the strain *B. bifidum* CNCM I-373 is thus approximately 3:4 after 7 d and 6:10 after 40 d at pH 4.0/5° C.

EXAMPLE 3

The procedure is as described in Example 1, except that *Bifidobacterium breve* CNCM I-374 is cultivated instead of *B. infantis* I-372.

A culture containing 1.2×10$^9$ living *B. breve* per cm$^3$ is obtained.

In the storage tests in acidified milk at pH 4.0/5° C., 0.87×10$^7$, 0.62×10$^7$ and 0.12×10$^7$ living *B. breve* per cm$^3$ of acidified milk are counted after 0 d, 7 d and 40 d, respectively. In other words, the survival level of the strain *B. breve* CNCM I-374 is approximately 7:10 after 7 d and approximately 14:100 after 40 d at pH 4.0/5° C.

COMPARISON EXAMPLE

A culture containing 4×10$^9$ *Bifidobacterium infantis* CNCM I-372 is prepared in the same way as described in Example 1. Normal cultures of *B. longum* (strain Bl 1) and *B. breve* (strain Bbr 2) respectively containing 2×10$^9$ and 1×10$^9$ living per cm$^3$ are similarly prepared. These cultures are said to be normal because they have resistances to acid which are similar to those of practically 99% of the bifidobacterium strains. Bl 1 and Bbr 2 are the references for identifying these strains within the collection of the depositor of strains CNCM I-372 to I-374.

0.8% by volume of these various cultures is added to separate batches of yogurts which are then stored in a refrigerator at 5° C. The amounts of bifidobacteria in these yogurts are counted after 0 d, 7 d and 21 d. The pH of the yogurts is also determined. The results obtained are set out in the following Table which illustrates the poor resistance to acid of normal cultures of bifidobacteria compared with that of the cultures according to the present invention.

| Storage at 5° C. d | B. longum (normal, Bl 1) | | B. breve (normal, Bbr 2) | | B. infantis (CNCM I-372) | |
|---|---|---|---|---|---|---|
| | pH | living bacteria cm$^3$ | pH | living bacteria cm$^3$ | pH | living bacteria cm$^3$ |
| 0 | 4.28 | $1.6 \times 10^7$ | 4.09 | $7.5 \times 10^6$ | 4.12 | $2.9 \times 10^7$ |
| 7 | 4.22 | $2.8 \times 10^6$ | 4.10 | $2.0 \times 10^3$ | 4.07 | $2.5 \times 10^7$ |
| 21 | 4.20 | $<1 \times 10^3$ | 4.06 | $<1 \times 10^3$ | 4.05 | $3.6 \times 10^7$ |

EXAMPLE 4

100 liters of cow's milk containing 3.5% by weight fats are pasteurized at 90° C. for 30 mins. and then cooled to 45° C. The milk is inoculated with 2% by volume of a culture of *Lactobacillus bulgaricus* and 2% by volume of a culture of *Streptococcus thermophilus* and then incubated for 3 h at 45° C. Approximately 100 liters of yogurt having a pH of 4.5 are thus obtained. The yogurt is cooled to 20° C., after which 3 liters of a culture of acid-resistant bifidobacteria prepared as described in Example 1 are added thereto with gentle stirring.

The yogurt thus obtained has the viscosity of a stirred yogurt and contains approximately $10^8$ living *B. infantis* per cm$^3$. This yogurt is filled in 0.15 liter pots and stored in a refrigerator for 5 weeks at 5° C. After this period of storage, more than $10^7$ living *B. infantis* per cm$^3$ of yogurt are counted.

EXAMPLE 5

100 liters of skimmed cow's milk are pasteurized for 30 mins. and then cooled to 32° C. The milk is inoculated with 1% by volume of a mixture of mesophilic lactic ferments (*S. cremoris, S. lactis, S. lactis deacetyllactis,* Leuconostoc) and then incubated for 16 h at 30° C.

Approximately 100 liters of a milk acidified to pH 4.4 and having the viscosity of a thick beverage of the buttermilk type are thus obtained. 5 liters of a culture of bifidobacteria prepared as described in Example 2 are added thereto.

A thick, acid milk-based beverage containing more than $10^7$ living *B. bifidum* per cm$^3$ is thus obtained. After filling in bottles and after storage in a refrigerator for 5 weeks at 8° C., more than $10^7$ living *B. bifidum* per cm$^3$ of beverage are again counted.

EXAMPLE 6

100 liters of whole cow's milk are homogenized, pasteurized at 155° C. for 2 s and then cooled to 40° C. The milk is then acidified to pH 4.2 by addition of lactic acid.

100 liters of coagulated milk are thus obtained. 5 liters of a culture of bifidobacteria prepared as described in Example 3 are added thereto with gentle stirring.

A coagulated milk having the viscosity of a stirred yogurt and containing $8 \times 10^7$ living *B. breve* per cm$^3$ is thus obtained. After packing in pots and after storage in a refrigerator for 5 weeks at 5° C., $2 \times 10^7$ living *B. breve* per cm$^3$ of coagulated milk are still counted.

EXAMPLE 7

100 liters of soya milk containing 8% by weight of dry matter of whole soya beans are sterilized at 150° C. for 5 s and then cooled to 37° C. 5 liters of a culture of bifidobacteria prepared as described in Example 2 are then added with stirring. The whole is then incubated for 10 h at 37° C. and cooled to 10° C.

A soya "yogurt" having a pH of 4.5 and containing $6 \times 10^9$ living *B. bifidum* per cm$^3$ is thus obtained. After storage for 5 weeks at 5° C., $2 \times 10^9$ living *B. bifidum* per cm$^3$ of this vegetable "yogurt" are still counted.

EXAMPLE 8

A whole cow's milk is pasteurized at 90° C. for 30 mins. and cooled to 37° C. 10% by volume of a culture of bifidobacteria obtained as described in Example 3 are added. The whole is incubated for 12 h at 37° C. and cooled to 10° C.

A "yogurt" having a pH of 4.5 and containing $5 \times 10^9$ living *B. breve* per cm$^3$ is thus obtained. After storage for 5 weeks at 5° C., $2 \times 10^9$ living *B. breve* per cm$^3$ of this "yogurt" are still counted.

I claim:

1. A process for preparing cultures containing acid resistant bifidobacteria comprising cultivating a bifidobacteria strain selected from a group consisting of *Bifidobacterium infantis* CNCM I-372, *Bifidobacterium bifidum*, CNCM I-373 and *Bifidobacterium breve* CNCM I-374 inoculated into a medium selected from a group consisting of a semisynthetic and synthetic lactic medium.

2. A process according to claim 1 wherein the medium is selected from a group consisting of a medium comprising whole cow's milk and skimmed cow's milk to which is added 0.1% to 2% by weight of yeast extract and 0.1% to 2% by weight of glucose, a medium comprising defatted soya milk and a medium comprising de Man, Rogasa and Sharpe agar ("MRS").

3. A process according to claim 1 wherein the medium is inoculated with approximately 3% to 10% by volume of an inoculum containing the bifidobacteria strain in an amount of approximately $10^8$ to $10^{10}$ per cm$^3$ of the inoculum and then the strain is cultivated in the medium for preparing the culture.

4. A process according to claim 3 wherein the bifidobacteria strain is cultivated at a temperature of from about 35° C. to about 42° C. for a period of time sufficient for providing the bifidobacteria in the culture in an amount of from $10^8$ to $10^{10}$ per cm$^3$.

5. The culture produced by the process of any one of claims 1-4.

6. A process for preparing food products containing acid resistant bifidobacteria comprising cultivating a bifidobacteria strain selected from a group consisting of *Bifidobacterium infantis* CNCM I-372, *Bifidobacterium bifidum* CNCM I-373 and *Bifidobacterium breve* CNCM I-374 inoculated into a medium selected from a group consisting of a semisynthetic and synthetic lactic medium for obtaining a culture of the strain and then adding the culture obtained to a food product and fermenting the food product for obtaining an acidified food product having a pH of from 4.0 to 4.6.

7. A process for preparing food products containing acid resistant bifidobacteria comprising cultivating a bifidobacteria strain selected from a group consisting of *Bifidobacterium infantis* CNCM I-372, *Bifidobacterium bifidum* CNCM I-373 and *Bifidobacterium breve* CNCM I-374 inoculated into a medium selected from a group consisting of a semisynthetic and synthetic lactic medium for obtaining a culture of the strain, acidifying a food product to a pH of from 4.0 to 4.6 and then adding the culture to the acidified food product.

8. A process according to claim 6 or 7 wherein the medium is selected from a group consisting of a medium comprising whole cow's milk and skimmed cow's milk to which is added 0.1% to 2% by weight of yeast extract and 0.1% to 2% by weight of glucose, a medium comprising defatted soya milk and a medium comprising MRS.

9. A process according to claim 6 or 7 wherein the medium is inoculated with approximately 3% to 10% by volume of an inoculum containing the bifidobacteria strain in an amount of approximately $10^8$ to $10^{10}$ per $cm^3$ of the inoculum and then the strain is cultivated in the medium at a temperature of from about 35° C. to about 42° C. for a period of time sufficient for providing the bifidobacteria in the culture in an amount of from $10^8$ to $10^{10}$ per $cm^3$.

10. A process according to claim 8 wherein the medium is inoculated with approximately 3% to 10% by volume of an inoculum containing the bifidobacteria strain in an amount of approximately $10^8$ to $10^{10}$ per $cm^3$ of the inoculum and then the strain is cultivated in the medium at a temperature of from about 35° C. to about 42° C. for a period of time sufficient for providing the bifidobacteria in the culture in an amount of from $10^8$ to $10^{10}$ per $cm^3$.

11. A process according to claim 6 or 7 wherein the culture obtained is added to a milk selected from a group consisting of animal and vegetable milk and which has been treated by a process selected from a group consisting of pasteurizing and sterilizing.

12. A process according to claim 8 wherein the culture obtained is added to a milk selected from a group consisting of animal and vegetable milk which has been treated by a process selected from a group consisting of pasteurizing and sterilizing.

* * * * *

UNITED STATES PATENT AND TRADEMARK OFFICE
CERTIFICATE OF CORRECTION

PATENT NO. : 4,870,020

DATED : September 26, 1989

INVENTOR(S) : Tomaso SOZZI

It is certified that error appears in the above-identified patent and that said Letters Patent is hereby corrected as shown below:

Column 3, line 24, "germs" should read --bacteria--.

Column 4, line 6, delete "germs of".

Column 5, line 38, "Leuconostoc" should be italicized.

Column 6, line 34, (line 5 of claim 1), after Bifidobacterium bifidum delete the coma.

Column 8, line 15, (line 3 of claim 11), after milk, delete "and".

Signed and Sealed this

Fourteenth Day of August, 1990

*Attest:*

HARRY F. MANBECK, JR.

*Attesting Officer*  *Commissioner of Patents and Trademarks*